(12) United States Patent
Takano et al.

(10) Patent No.: US 7,223,559 B2
(45) Date of Patent: May 29, 2007

(54) **PLASMIDS FOR CHROMOSOMAL RECOMBINATION OF *ESCHERICHIA COLI***

(75) Inventors: Junicho Takano, Cape Girardeau, MO (US); Kuniki Kino, Chiba (JP); Satoru Furukawa, Chesterfield, MO (US)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 262 days.

(21) Appl. No.: 10/240,712

(22) PCT Filed: Apr. 6, 2001

(86) PCT No.: PCT/JP01/02980

§ 371 (c)(1),
(2), (4) Date: Oct. 4, 2002

(87) PCT Pub. No.: WO01/77345

PCT Pub. Date: Oct. 18, 2001

(65) Prior Publication Data

US 2003/0049846 A1    Mar. 13, 2003

(30) Foreign Application Priority Data

Apr. 6, 2000    (JP) .............................. 2000-105086

(51) Int. Cl.
*C12P 21/02*    (2006.01)
(52) U.S. Cl. ..................... 435/69.1; 435/41; 435/91.1; 435/320.1; 435/252.33; 435/488
(58) Field of Classification Search ............ 435/320.1, 435/69.1, 325, 6
See application file for complete search history.

(56) References Cited

U.S. PATENT DOCUMENTS 4,743,546 A    5/1988    Backman et al.

OTHER PUBLICATIONS

Chen et al. L-(+)-Lactate Dehydrogenase Deficiency is Lethal is Streptococcus mutans J. Bacter. vol. 176 No. 5 1994 pp. 1542-1545.*

Martinez-Morales et al. Chromosomal integration of heterologous DNA in *E. coli* with precise removal of markers and replicons used during construction. J. Bacteriol. Nov. 1999 vol. 181 No. 22 pp. 7143-7148.*

Furukawa et al. Breeding of L-threonine hyper-producer of *E. coli* W Appl. Microb. Biotechnol 1988vol. 29 253-257).*

Zinder, Norton, et al. "Genetic Exchange in *Salmonella*", *J. Bact.*, vol. 64 (1952), 679-99.

Chen, Anping, et al., "L-(+)-Lactate Dehydrogenase Definiciency is Lethal is *Streptococus mutans*", *J. Bact.*., vol. 176, No. 5, (1994), 1542-45.

Hashimoto, Tamotsu, et al., "Isolation of Temperature-Sensitive Mutants of R Plasmid by In Vitro Mutagenesis with Hydroxylamine", *J. Bact*.., vol. 127, No. 3, (1976), 1561-63.

Furukawa, Satoru, et al., Breeding of L-threonine hyper-producer of *Escherichia coli* W, *App. Micro and Biotech.*, vol. 29 (1988) 253-7.

Gleiser, I.E., "Growth of *E. coli* W to High Cell Concentration by Oxygen Level Linked Control of Carbon Source Concentration", *Biotech. and Bioeng.*, vol. 23, (1981), 1015-21.

Kulakauskas, S., et al., "Efficient Introduction of Cloned Mutant Alleles into the *Escherichia coli* Chromosome", *J. Bact.*., vol. 173, No. 8, (1991) 2633-8.

Le Borgne, S., et al., "pBRINT-$T_s$: a plasmid family with a temperature-sensitive replicon, designed for chromosomal integration into the *lacZ* gene of *Escherichia coli*", *Gene*, vol. 223 (1998) 213-9.

* cited by examiner

*Primary Examiner*—James Ketter
(74) *Attorney, Agent, or Firm*—Fitzpatrick, Cella, Harper & Scinto

(57) ABSTRACT

A temperature-sensitive plasmid which is capable of autonomous replication in *Escherichia coli* K-12 at 10–30° C., but, at a temperature of 33° C. or more, is incapable of autonomous replication in *Escherichia coli* K-12 or is distributed unhomogeneously upon the cell division of *Escherichia coli* K-12, thereby not to be stably carried within cells of *Escherichia coli* K-12 under said temperature, and which is incapable of autonomous replication in a microorganism belonging to the genus *Escherichia* other than *Escherichia coli* K-12 or is distributed unhomogeneously upon cell division of said microorganism at any temperature, thereby not to be stably carried within cells of said microorganism.

22 Claims, 2 Drawing Sheets

US 7,223,559 B2

PLASMIDS FOR CHROMOSOMAL RECOMBINATION OF *ESCHERICHIA COLI*

TECHNICAL FIELD

The present invention relates to a plasmid to be used for integrating genes into a microorganism belonging to the genus *Escherichia* other than *Escherichia coli* K-12, a method for integrating the genes into the chromosome, a recombinant strain constructed according to the method, and a method for producing useful substances by using the recombinant strain.

BACKGROUND ART

When a microorganism engineered to intracellularly carry a plasmid that expresses a specific gene is utilized for the production of a useful substance, over-expression of the gene and instability of the plasmid often cause problems. To solve the problems, modifications of genes on a chromosome are carried out as an effective method. Methods involving mutagenic treatments have long been carried out as a chromosomal engineering technique in *Escherichia coli*. This method is directed to the selection of a desired mutant strain from randomly mutated strains, and requires a great deal of work. In addition, deliberate or rational manipulation is almost impossible.

On the other hand, P1 transduction using P1 phage is known to be the most versatile technique to deliberately and rationally manipulate the chromosome of *Escherichia coli* [Zinder, N. D. and Lederberg J., J. Bacteriol., 64, 679 (1952)].

Chromosomal manipulation techniques other than P1 transduction are roughly classified into 2 types.

One type is directed to a method which comprises inserting a gene of interest into a plasmid capable of autonomous replication in microorganisms other than *Escherichia coli* but incapable of autonomous replication in *Escherichia coli* and transforming *Escherichia coli* with the plasmid to obtain a strain in which the gene of interest is integrated into its chromosome according to the principle of homologous recombination [A. Chen et al., J. Bacteriol., 176, 1542 (1994)]. However, this method involves a drawback that a desired chromosomal recombinant strain is obtained only at a very low frequency because a plasmid which has been prepared by using a microorganism other than *Escherichia coli* as a host cell, is decomposed by restriction enzymes within *Escherichia coli*.

The other type is directed to the method in which a plasmid being capable of autonomous replication under the normal growth conditions in *Escherichia coli* K-12 but incapable of autonomous replication under certain conditions such as a high temperature condition is used and a gene of interest is integrated into a chromosome in accordance with the principle of homologous recombination [T. Hashimoto, and M. Sekiguchi, J. Bactereiol., 127, 1561 (1976)].

*Escherichia coli* that have been widely used in the research and industrial areas include several types such as the K-12, B, and W strains. Many of the genetic recombination techniques have been developed by using the K-12 strain.

*Escherichia coli* W is suitable for the production of useful substances such as amino acids, etc. [S. Furukawa et al., Appl. Microbiol. Biotechnol., 29, 253 (1988)] and serves many uses in fermentative production as it assimilates sucrose and has been actually subjected to high density cell culture successfully [I. E. Gleiser and S. Bauer, Biotechnol. Bioeng., 23, 1015 (1981)].

The above-mentioned genetic engineering techniques relate to the K-12 strain and no report has so far been made that concerns with microorganisms belonging to the genus *Escherichia* of the types, different from K-12.

DISCLOSURE OF THE INVENTION

The object of the present invention is to establish a new chromosomal recombination technique in microorganisms belonging to the genus *Escherichia* other than the K-12 strain and solve the above problems.

The present invention relates to the following (1)–(14).

(1) A temperature-sensitive plasmid which is capable of autonomous replication in *Escherichia coli* K-12 at 10–30° C., but at a temperature of 33° C. or more, is incapable of autonomous replication in *Escherichia coli* K-12 or is distributed unhomogeneously upon the cell division of *Escherichia coli* K-12, thereby not to be stably carried within cells of *Escherichia coli* K-12 under said temperature, and which is incapable of autonomous replication in a microorganism belonging to the genus *Escherichia* other than *Escherichia coli* R-12 or is distributed unhoinogeneously upon cell division of said microorganism at any temperature, thereby not to be stably carried within cells of said microorganism.

(2) The plasmid according to the above (1), wherein the microorganism belonging to the genus Escherichia other than *Escherichia coli* K-12 is *Escherichia coli* W or *Escherichia coli* B.

(3) The plasmid according to the above (1) or (2), wherein the plasmid is a plasmid containing a DNA fragment capable of undergoing homologous recombination with the chromosome of *Escherichia coli*.

(4) The plasmid according to any one of the above (1) to (3), wherein the plasmid is carried by *Escherichia coli* DH5α/pMTS11910 (FERM BP-6904) or *Escherichia coli* DH5α/pMTS11914 (FERM BP-6905).

(5) A plasmid having one or more genes integrated therein, which is obtainable by integrating any genes into the plasmid according to any one of the above (1) to (4).

(6) A method for integrating one ore more genes, which comprises introducing the plasmid according to any one of the above (1) to (5) to a microorganism belonging to the genus *Escherichia* other than *Escherichia coli* K-12.

(7) The method for integrating one or more genes according to the above (6), wherein the microorganism belonging to the genus *Escherichia* other than *Escherichia coli* K-12 is *Escherichia coli* W or *Escherichia coli* B.

(8) The method for integrating one or more genes according to the above (6) or (7), wherein the integration of the genes is an integration genes in which the plasmid is integrated into a chromosome.

(9) The method for integrating one or more genes according to any one of the above (6) to (8), wherein the integration of one or more genes is an integration in which a DNA fragment on the plasmid is substituted with a DNA fragment on a chromosome by homologous recombination.

(10) A transformant obtainable by the method according to any one of the above (6) to (9).

(11) The transformant according to the above (10), wherein the transformant is a transformant selected from the group consisting of *Escherichia coli* DH5α/pMTS11910 (FERM BP-6904), *Escherichia coli* DH5α/pMTS11914

(FERM BP-6905), *Escherichia coli* WLA-131 (FERM BP-6902), and *Escherichia coli* WL-1133 (FERM BP-6903).

(12) A method for producing a useful substance, which comprises culturing the transformant according to the above (10) or (11) in a medium, allowing the useful substance to produce and accumulate in a culture and recovering the useful substance from the culture.

(13) The method according to the above (12), wherein the useful substance is selected from the group consisting of amino acids, organic acids, nucleic acids, nucleic acid-related substances, sugars, lipids, vitamins, and pigments, and derivatives thereof.

(14) The method for producing a useful substance according to the above (12), wherein the useful substance is a protein.

[1] Mutagenic Treatment of Plasmid

As the plasmid, pMW119 (available from Nippon Gene Co., Ltd.) or a plasmid having the same ori region and the rep gene as those of pMW119 is used. An ori region is a region containing the initiation site of replication and the rep gene is a gene encoding replicase.

Mutagenic treatment of the plasmid is carried out according to a known method using hydroxylazine [G. O. Humphreys et al., Mol. Gen. Genet., 145, 101 (1976)], etc.

For example, when hydroxylamine is used, the plasmid can be mutated by dissolving about 10 μg of the plasmid in phosphate buffer [50 mmol/l $NaH_2PO_4$, 1 mmol/l EDTA2Na, pH 6.0 (NaOH)] containing 0.4 mol/l hydroxylamine hydrochloride, and heating the solution at 75° C. for 30 to 60 minutes.

(2) Preparation of Temperature-sensitive Plasmids

A plasmid showing temperature-sensitivity in *Escherichia coli* K-12 can be obtained by a known method [T. Hashimoto, and M. Sekiguchi, J. Bacteriol., 127, 1561 (1976)].

More particularly, *Escherichia coli* K-12 is transformed with the plasmid to which a mutagenic treatment has been given to obtain a strain having resistance to a drug such as ampicillin within the range of 10–32° C. While any method of transformation that can transform *Escherichia coli* K-12 may be used, electroporation [W. J. Dower et al., Nucleic Acids Res., 16, 6127 (1988)] that offers high transformation efficiency is preferred.

*Escherichia coli* K-12 to which a transformation treatment has been given is spread on LB agar medium [1.0% Bacto Tryptone (Difco), 0.5% Yeast Extract (Difco), 1.0% NaCl 2% agar] containing a drug to be used as a marker and cultured at 10–32° C. for 6–24 hours.

Strains whose growth is confirmed by the culturing are selected as transformants. The transformants are cultured on an agar medium without containing any drug added at a temperature of 33° C. or more at which the transformants can grow.

After the culturing, strains grown are spread on an agar medium containing a drug such as ampicillin and cultured at a temperature of 33° C. or more at which the strains can grow for 6–24 hours. Strains corresponding to those that can not grow under these conditions are separated from the above agar medium without containing any drug added and cultured again on the medium without containing any drug added. After the culturing, a plasmid is separated from the strains according to a conventional method. The plasmid is the temperature-sensitive plasmid.

[3] Preparation of Plasmids Incapable of Autonomous Replication in the Cells of a Microorganism Belonging to the Genus Escherichia Other Than *Escherichia coli* K-12

The plasmid of the present invention, that is, the plasmic incapable of replication in the cells of a microorganism belonging to the genus *Escherichia* other than *Escherichia coil K-* 12, can be selected from plasmids showing temperature sensitivity in *Escherichia coli K*-12, which are obtained according to the method described in (2) above.

The microorganisms belonging to the genus *Escherichia*other than *Escherichia coli* K-12 herein may be any microorganisms that belong to the genus *Escherichia* other than the K-12 type strain. Examples thereof include microorganisms belonging to *Escherichia coli* of such types as *Escherichia coli* W, *Escherichia coli* B, *Escherichia coli* C, *Escherichia coli* 15, etc. and *Escherichia coli* W or *Escherichia coli* B is preferred.

More particularly, transformation of a microorganism belonging to the genus Escherichia other than *Escherichia coli* K-12 is carried out by using the plasmid that shows temperature sensitivity in *Escherichia coli* K-12 to obtain transformants. If the transformants are unable to grow at any temperature when they are cultured in a medium containing a drug, such temperature-sensitive plasmid is the plasmid having the property of the present invention.

[4] Integration of a Gene into a Chromosome

The plasmid which can not replicate in a microorganism belonging to the genus *Escherichia* other than *Escherichia coli* K-12 at any temperature obtained in accordance with the above-described method (hereinafter referred to as the plasmid of the present invention) is used for integration into a chromosome.

First, a gene is cloned to the plasmid of the present invention. The gene may be any gene that participates in the production of a desired useful substance and has a sequence homologous to a gene of interest in the chromosome of a microorganism belonging to the genus *Escherichia* other than *Escherichia coli* K-12. The useful substance may be any useful substance so far as the gene participates in the production thereof. For example, amino acids such as leucine, etc., organic acids such as isocitric acid, etc., nucleic acids or nucleic acid-related substances such as flavin adenine dinucleotide, etc., sugars such as fructose, etc., lipids such as phospholipid, glycolipid, etc., vitamins such as biotin, etc., and pigments such as carotene, etc., derivatives thereof, proteins such as enzymes encoded by the gene, etc. may be mentioned but the useful substances are not limited to these substances.

Cloning of the gene can be carried out from *Escherichia coli* K-12 according to a known method [Molecular Cloning, A Laboratory Manual, Second Edition, Cold Spring Harbor Laboratory Press (1989)] (hereinafter referred to as Molecular Cloning, Second Edition). Furthermore, it is possible to artificially modify the nucleotide sequence of the cloned gene according to a known method (Molecular Cloning, Second Edition). For the cloning of the gene and modification of the cloned gene, *Escherichia coli* K-12 is used as a host cell and culturing is carried out at 32° C. or less.

The thus constructed recombinant plasmid is used to transform a microorganism belonging to the genus *Escherichia* other than *Escherichia coli* K-12 and the strain is cultured on a medium containing a drug such as ampicillin to obtain a drug resistance strain, whereby chromosomal recombinant strain in which plasmid containing the gene of interest has been integrated into the chromosome can be obtained. To transform the microorganism, any of known methods such as electroporation, calcium chloride method (Molecular Cloning, Second Edition), etc. can be used.

It is also possible to obtain a strain in which the gene cloned on the plasmid is substituted with the gene originally carried by a microorganism belonging to the genus *Escherichia* other than *Escherichia coli* K-12 on its chromosome.

More particularly, a strain transformed with the plasmid of the present invention is cultured on a medium without containing a drug such as ampicillin. Either a solid agar medium or a liquid medium without containing agar may be used for the culturing so far as the transformants can grow thereon.

The cultured cell is properly diluted with sterilized physiological saline, spread on LB agar medium without containing a drug such as ampicillin, and cultured. Each of the colonies grown is spread on an agar medium containing a drug such as ampicillin and the strains corresponding to the strains that have not grown are separated from the original medium without containing a drug. From the separated strains, the strain in which the gene on the plasmid of the present invention and the gene originally present on the chromosome of a microorganism belonging to the genus *Escherichia* other than *Escherichia coli* K-12 are substituted by homologous recombination can be selected.

The chromosomal recombinant strain in which the plasmid containing a gene of interest is integrated into its chromosome or the strain in which the gene originally carried by a microorganism belonging to the genus *Escherichia* other than *Escherichia coli* K-12 is substituted with the gene cloned on the plasmid is hereinafter referred to as the microorganism of the present invention.

By using the microorganism of the present invention, useful substances can be produced.

In the above method, if the integration of the plasmid on the chromosome is designed so that the site of integration is in the nucleotide sequence of a target gene, it is possible to disrupt the target gene by inserting a new sequence to the target gene. The gene disruption according to this method has an advantage of higher reliability as compared with inactivation of a gene by mutation.

For the culturing of the microorganism of the present invention, any of natural media and synthetic media may be used so far as it is a medium that enables efficient culturing of the microorganism of the present invention which contains carbon sources, nitrogen sources, inorganic salts, etc. which can be assimilated by the microorganism of the present invention.

As the carbon sources, any carbon sources that can be assimilated by the microorganism of the present invention can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of various organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is carried out under aerobic conditions, for example, by shaking culture or submerged spinner culture under aeration.

The suitable culturing temperature is 15–40° C. and the culturing period is usually 16 hours to 7 days. The pH is maintained preferably at 3.0–9.0 during the culturing. The pH adjustment is carried out using an organic or inorganic acid, an alkali solution, urea, calcium carbonate, ammonia, etc.

If necessary, antibiotics such as ampicillin, tetracycline, etc. may be added to the medium during the culturing.

By the culturing in the above manner, a useful substance can be accumulated in the culture. After the completion of culturing, the useful substance can be recovered from the culture by removing precipitates such as the cell and using a combination of various methods such as ion exchange treatment, condensation, salting-out, etc.

When the useful substance is a protein, the protein can be isolated and purified by conventional methods for isolating and purifying proteins. For example, when the protein is expressed in a soluble form in the cells, after the completion of culturing, the cells are recovered by centrifugation and suspended in an aqueous buffer, followed by disruption using a sonicator, French press, Manton Gaulin homogenizer, Dynomill or the like to obtain a cell-free extract. A purified protein can be obtained from the supernatant obtained by centrifuging the cell-free extract, by using conventional methods for isolation and purification of proteins such as extraction with a solvent, salting-out with ammonium sulfate, etc., desalting, precipitation with an organic solvent, anion exchange chromatography using resins such as diethylaminoethyl(DEAE)-Sepharose and DIAION HPA-75 (Mitsubishi Kasei corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography, chromatofocusing, electrophoresis such as isoelectric focusing, or the like alone or in combination.

When the protein is expressed as an inclusion body in cells, the cells are similarly recovered and disrupted, followed by centrifugation to obtain the inclusion body of the protein as a precipitate fraction. The inclusion body of the protein recovered is solubilized with a protein-denaturing agent. The solubilized protein solution is diluted or dialyzed to reduce the concentration of the protein-denaturing agent contained in the solubilized protein solution, whereby the normal steric structure of the protein is restored. Then, a purified protein preparation can be obtained through the same isolation and purification procedures as mentioned above.

Examples of the present invention are shown below. These examples are not to be construed as limiting the scope of the invention.

BEST MODES FOR CARRYING OUT THE INVENTION

Figure 1:
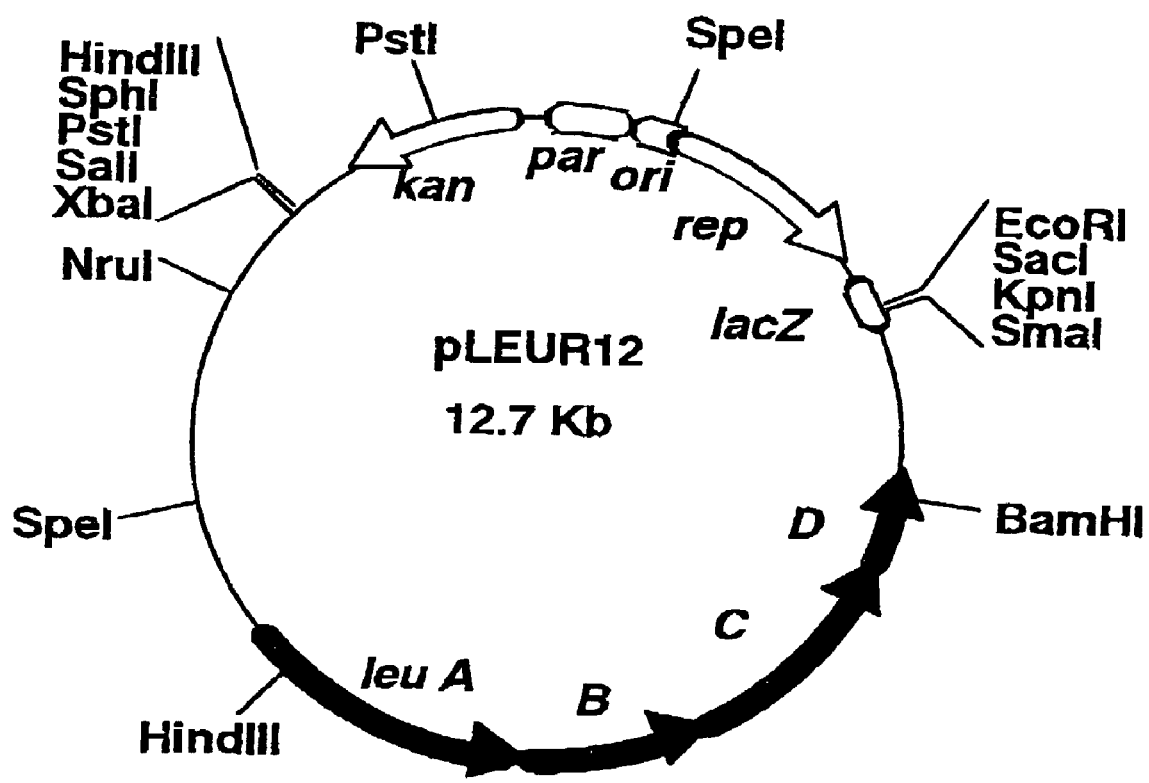
FIG. 1 is a diagram showing a restriction map of pLEUR12 containing leu operon and distribution of each gene in the leu operon presumed from the information on *Escherichia coli* K-12.

Unless otherwise noted, the operations in the following examples were carried out according to the description of Molecular Cloning, Second Edition.

EXAMPLE 1

Preparation of Plasmid Which is not Maintained in *Escherichia coli* W

A typical plasmid vector of *Escherichia coli*, pMW119 (product of Nippon Gene Co., Ltd.), was subjected to an in vitro mutagenic treatment. The mutagenic treatment was carried out according to the following method using hydroxylamine described in G. O. Humphreys et al., Mol. Gen. Genet., 145, 101 (1976).

About 10 μg of pMW119 prepared by ultracentrifugation was dissolved in phosphate buffer [50 mmol/l $NaH_2PO_4$, 1 mmol/l EDTA2Na, pH 6.0 (NaOH)] containing 0.4 mol/l hydroxylamine hydrochloride. The solution was heated at 75° C. for 40 min. Thereafter, the treated DNA was precipitated by the addition of ethanol and dissolved in TE solution [10 mmol/l tris(hydroxymethyl)methane, 1 mmol/l EDTA2Na, pH 8.0 (HCl)].

*Escherichia coli* K-12 DH5α (Bethesda Research Laboratories) was transformed using the DNA solution. The strain was cultured on LB agar medium [1% Bacto Tryptone (Difco), 0.5% yeast extract, 0.5% NaCl, 2% agar] containing 50 mg/l ampicillin at 30° C. and about 1700 strains grown were selected.

The selected strains were replicated on LB agar medium without containing ampicillin and cultured at 42° C. The colonies grown were again replicated on LB agar medium containing ampicillin and cultured at 42° C. and 22 strains that could not grow were selected from the original plate.

By using the plasmid extracted from the selected strains, *Escherichia coli* W (ATCC-11105) and *Escherichia coli* B (ATCC-11303) were transformed by electroporation [William J. Dower et al., Nucleic Acids Research, 16, 6127 (1988)]. In this case, the transformation efficiency was $7 \times 10^8$ cells/μg of pBR322.

In each of the W and B strain, two kinds of plasmids by which transformants showing resistance to ampicillin were obtained at a frequency of $1/10^7$ or less in comparison to the frequency with pMW119 to obtain such transformants were respectively named pMTS11910 and pMTS11914. *Escherichia coli* DH5α was transformed with pMTS11910 or pMTS11914. The transformants, *Escherichia coli* DH5α/pXTS11910 and *Escherichia coli* DH5α/pMTS11914, have been deposited under the Budapest Treaty with National Institute of Advanced Industrial Science and Technology, International Patent Organism Depositary: Tsukuba Central 6, 1-1-1 Higashi, Tsukuba, Ibaraki, Japan (former Agency of Industrial Science and Technology, National Institute of Bioscience and Human-Technology: 1-1-3 Higashi, Tsukuba, Ibaraki, Japan) as of Sep. 30, 1999 as FERM BP-6904 and FERM BP-6905, respectively.

EXAMPLE 2

Construction of Temperature-sensitive Plasmid Containing Leu Operon

As a gene to be subjected to chromosomal gene integration, leu operon of an L-leucine producing *Escherichia coli* strain (FERM BP-4704)(Japanese Published Unexamined Patent Application No. 70879/96) was used. Chromosomal DNA of the FERM BP-4704 strain was extracted according to the method of Saito et al. [H. Saito and K. Miura, Siochem. Biophys. Acta, 72, 619 (1963)] and the chromosomal DNA was partially decomposed with restriction enzyme Sau3AI. On the other hand, pMW218 (Nippon Gene Co., Ltd.) was decomposed with restriction enzyme BamHI and treated with alkali phosphatase. The DNA solutions thus treated were mixed and subjected to ligation reaction with T4 DNA ligase.

By using the DNA undergoing the ligation treatment, an L-leucine requiring *Escherichia coli* strain, CV437 [M. G. Davis and J. M. Calvo, J. Bacteriol., 129, 1078 (1977)], was transformed by electroporation. As a result, 66 strains showing kanamycin resistance and L-leucine non-requirement were obtained. The L-leucine non-requiring strains were obtained by selecting strains that could grow when cultured on M9 minimal medium without containing L-leucine.

From these strains, 12 strains were selected at random and the plasmid DNA was extracted. By using the plasmid DNA, an L-leucine requiring strain, CV524 [M. G. Davis and J. M. Calvo, J. Bacteriol., 129, 1078 (1977)] was transformed by electroporation and the plasmid from which L-leucine non-requiring strains were obtained was named pLEUR12. Since the CV437 strain is deficient in leu A and the CV524 strain in leu D, it was presumed that leu operon at least containing leu A and leu D was inserted to pLECR12. Furthermore, a restriction map of the DNA fragment inserted to pLEUR12 as prepared coincides with the map corresponded with that of leu ABCD gene of *Escherichia coli* K-12 whose nucleotide sequence has already been determined [T. Ura et al., Nucleic Acids Research, 20, 3305 (1992)].

The structure of pLEUR12 presumed is shown in FIG. 1.

The cloned leu operon was inserted to pMTS11914 according to the following procedures.

First, pLEUR12 was cleaved with restriction enzymes EcoRI and XbaI, the cleaved DNA fragments were subjected to agarose gel electrophoresis, and an about 9 kb fragment containing leu operon was extracted from the gel.

Figure 2:
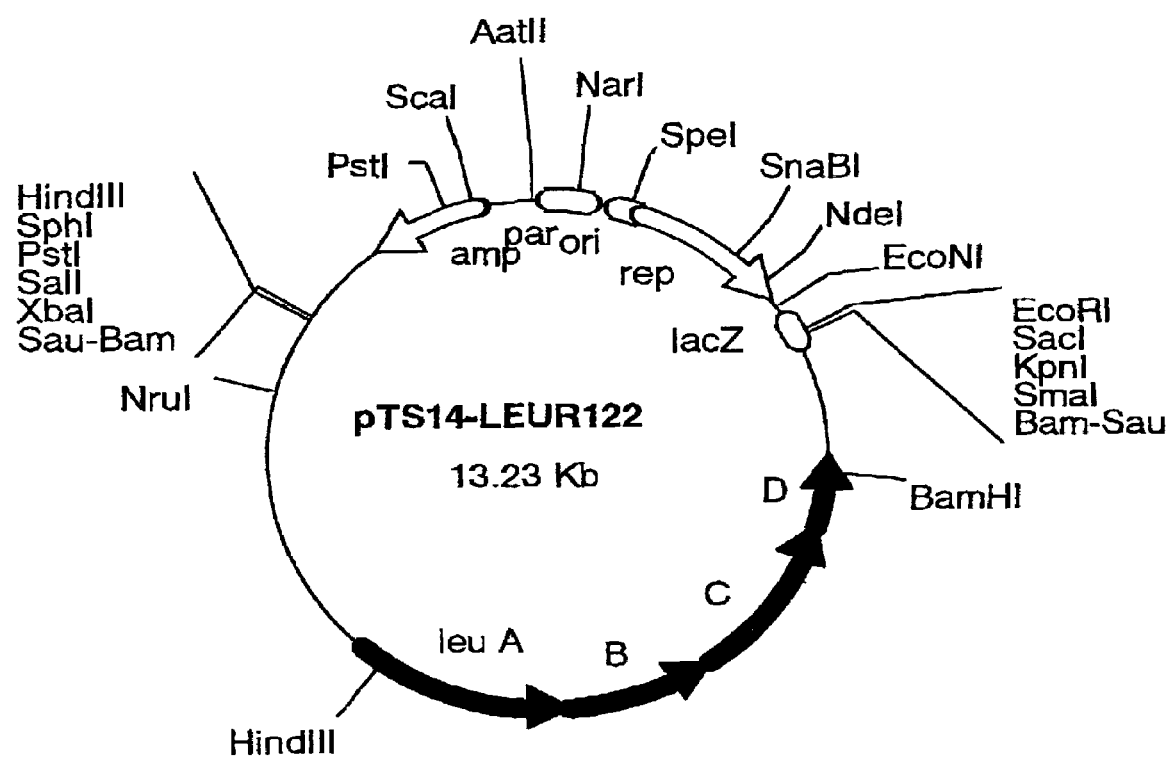
FIG. 2 is a diagram showing a restriction map of pTS14-LEUR122 containing leu operon and distribution of each gene.

Separately, pMTS11914 was cleaved with restriction enzymes EcoRI and XbaI and further treated with alkali phosphatase. The treated DNA solutions were mixed and subjected to ligation reaction with T4 DNA ligase. By using the DNA undergoing the ligation treatment, an L-leucine requiring *Escherichia coli* strain, C600 [Brenner S., and J. R. Beckwith, J. Mol. Biol., 13, 629 (1965)], was transformed by electroporation. As a result, about 500 ampicillin resistance strains were obtained. From these ampicillin resistance strains, L-leucine non-requiring strains were selected in accordance with the method described above, and cultured at 42° C. and strains showing sensitivity to ampicillin were selected. Plasmid was extracted from the selected strains, the cleavage pattern of the plasmid with restriction enzymes was examined and the plasmid to which the desired leu operon was inserted was named pTS14-LEUR122 (FIG. 2).

EXAMPLE 3

Integration of pTS14-LEUR122 into the Chromosome of *Escherichia coli* W

*Escherichia coli* W 113-3 [ATCC-11105, J. Bcteriol., 60, 17 (1950)] was transformed with pTS14-LEUR122 by electroporation. Whether or not the ampicillin-resistant strains obtained by the transformation had the L-leucine productivity was examined by the bioassay method.

More particularly, the ampicillin-resistant strains obtained were spread on M9 minimal agar medium (5 g/l glucose, 6 g/l Na$_2$HPO$_4$, 3 g/l KH$_2$PO$_4$, 0.5 g/l NaCl, 1 g/l NH$_4$Cl, 1 mmol/l MgSO$_4$, 0.1 mmol/l CaCl$_2$, 20 mg/l DL-methionine, 2% agar) containing the above-described L-leucine requiring strain CV524 at a concentration of about 1×10$^7$ cells/ml and cultured at 37° C. for 12 hours.

Around the strains having L-leucine productivity, the CV524 strain was grown and a white-turbid circle (hereinafter called halo) was formed. Strains forming a halo bigger than the average size of the halos formed were separated and cultured on LB agar medium containing ampicillin at 42° C. Among these strains, those showing resistance to ampicillin were selected as strains in which pTS14-LEUR122 was integrated into the chromosome and one of such strains was named *Escherichia coli* WLA-131.

It was confirmed by southern hybridization that pTS14-LEUR122 was integrated into *Escherichia coli* WLA-131 on its chromosome by homologous recombination.

*Escherichia coli* WLA-131 has been deposited under Budapest Treaty with National Institute of Advanced Industrial Science and Technology, International Patent Organism Depositary: Tsukuba Central 6, 1-1-1 Higashi, Tsukuba, Ibaraki, Japan (former Agency of Industrial Science and Technology, National Institute of Bioscience and Human-Technology: 1-1-3 Higashi, Tsukuba, Ibaraki, Japan) as of Sep. 30, 1999 as FERM BP-6902.

EXAMPLE 4

Preparation of a Strain Having Substitution from the Chromosomally Integrated Strain

*Escherichia coli* WLA-131 was inoculated into 5 ml of LB medium and cultured with shaking at 33° C. for 24 hours. The resulting culture (100 μl) was again inoculated into 5 ml of LB medium and cultured with shaking at 33° C. for 24 hours.

The culture was properly diluted and spread on LB agar medium.

The colonies grown were replicated on LB agar medium containing or without containing ampicillin to select ampicillin-sensitive strains. L-leucine productivity of the ampicillin-sensitive strains was examined according to the bioassay method described in Example 3 and one of the strains that formed a halo was named *Escherichia coli* WLA-1133.

*Escherichia coli* WLA-1133 has been deposited under the Budapest Treaty with National Institute of Advanced Industrial Science and Technology, International Patent Organism Depositary: Tsukuba Central 6, 1-1-1 Higashi, Tsukuba, Ibaraki, Japan (former Agency of Industrial Science and Technology, National Institute of Bioscience and Human-Technology: 1-1-3 Higashi, Tsukuba, Ibaraki, Japan) as of Sep. 30, 1999 as FERM BP-6903.

To confirm that the gene on the chromosome of *Escherichia coli* WLA-1133 was recombined as intended, analysis by southern hybridization was carried out. That is, pLEUR12 was digested with HindIII and BamHI to obtain a 4.4 kb fragment containing leu ABCD. The fragment was modified with digoxigenin and used as a probe. Chromosomal DNA was extracted from *Escherichia coli* W113-3, *Escherichia coli* WLA-131 and *Escherichia coli* WL-1133, decomposed with SacII and KpnI and subjected to agarose gel electrophoresis.

After the electrophoresis, the separated DNA was transferred to a nitrocellulose membrane and subjected to hybridization with the probe, followed by color development operation. In *Escherichia coli* W113-3 and *Escherichia coli* WL-1133 which are the parent strains, only an about 17 kb fragment containing leu ABCD was detected. On the other hand, in *Escherichia coli* WLA-131, two 11 kb and about 19 kb fragments were detected. pTS14-LEUR122 which was used for integration into the chromosome contains one KpnI site in its multi-cloning site. Therefore, if leu operon on the plasmid was integrated on the chromosome by homologous recombination as we presumed, two 19 kb and 11 kb fragments should be detected. Thus, it could be confirmed that *Escherichia coli* WLA-131 carries pTS14-LEUR122 integrated on leu operon on its chromosome and that in *Escherichia coli* WL-1133, the integrated plasmid is missing by repeated homologous recombination.

That is, pMTS11914-derived region of pTS14-LEUR122 integrated on the chromosome is missing from the chromosome and one copy of leu operon is present on the chromosome of *Escherichia coli* WL-1133.

EXAMPLE 5

Amino Acid Production Test

*Escherichia coli* W113-3, *Escherichia coli* WLA-131, and *Escherichia coli* WL-1133 were respectively inoculated into 20 ml of a seed medium (2% glucose, 1% peptone, 1% yeast extract, 0.25% NaCl, pH 7.0) in a 250-ml Erlenmeyer flask and cultured with shaking at 30° C. for 16 hours. The obtained seed cultures (2.5 ml each) were respectively inoculated into 25 ml of a production medium (3% glucose, 1.6% ammonium sulfate, 0.1% potassium dihydrogenphosphate, 0.2% corn steep liquor, 150 mg/l DL-methionine, 4% trimagnesium phosphate, 1% calcium carbonate, pH 7.0) in a 250-ml Erlenmeyer flask and cultured with shaking at 30° C. for 48 hours. Accumulation of L-leucine in the culture after the completion of culturing was quantitatively determined by high performance liquid chromatography.

The results are shown in Table 1.

TABLE 1

| Strain | Leu (mg/l) |
|---|---|
| *Escherichia coli* W113-3 | 0 |
| *Escherichia coli* WLA-131 | 151 |
| *Escherichia coli* WL-1133 | 145 |

INDUSTRIAL APPLICABILITY

By using a plasmid which is capable of autonomous replication in *Escherichia coli* K-12 but incapable of autonomous replication in *Escherichia coli* other than *Escherichia coli* K-12 (microorganisms belonging to the genus *Escherichia* other than *Escherichia coli* K-12), it is possible to integrate genes of interest in any region on the chromosome of microorganisms belonging to the genus *Escherichia* other than *Escherichia coli* K-12 or to effectively modify genes of interest on the chromosome.

The invention clamied is:

1. A temperature-sensitive plasmid (i) which is obtainable from a plasmid carried by *Escherichia coli* DH5 α/pMTS11910 (FERM BP-6904) or *Escherichia coli* DH5 α/pMTS11914 (FERM BP-6905), (ii) which autonomously replicates in *Escherichia coli* K-12 at 10–30° C., (iii) at a temperature of 33° C. or more, is incapable of autonomous replication or is distributed unhomogeneously upon cell division of *Escherichia coli* K-12, and so is not stably carried within *Escherichia coli* K-12, and (iv) does not autonomously replicate or is distributed unhomogeneously in an *Escherichia* other than *Escherichia coli* K-12 at any temperature, and so is not stably carried within said *Escherichia* other than *Escherichia coli* K-12.

2. The plasmid according to claim 1, wherein the *Escherichia* other than *Escherichia coli* K-12 is *Escherichia coli* W or *Escherichia coli* B.

3. The plasmid according to 2, wherein the plasmid contains a DNA fragment capable of undergoing homologous recombination with the chromosome of *Escherichia coli*.

4. A plasmid, comprising the plasmid according to any one of claims 1 to 3, said plasmid having one or more genes integrated therein.

5. A method for integrating, which comprises introducing the plasmid according to claim 4 to a microorganism belonging to the genus *Escherichia* other than *Escherichia coli* K-12, wherein said one or more genes are integrated into said microorganism belonging to the genus *Escherichia* other than *Escherichia coli* K-12.

6. The method for integrating one or more genes according to claim 5, wherein the *Escherichia* microorganism other than *Escherichia coli* K-12 is *Escherichia coli* W or *Escherichia coli* B.

7. The method for integrating one or more genes according to claim 5, wherein the plasmid is integrated into a chromosome.

8. The method for integrating one or more genes according to claim 7, wherein a DNA fragment on the plasmid is substituted with a DNA fragment on a chromosome by homologous recombination.

9. A transformant obtained by the method according to claim 7.

10. The transformant according to claim 9, wherein the transformant is a transformant selected from the group consisting of *Escherichia coli* DH5α/pMTS11910 (FERM BP-6904), *Escherichia coli* DH5α/pMTS11914 (FERM BP-6905), *Escherichia coli* WLA-131 (FERM BP-6902), and *Escherichia coli* WL-1133 (FERM BP-6903).

11. A method for producing a useful substance, which comprises culturing the transformant according to claim 9 in a medium, allowing the useful substance to produce and accumulate in a culture and recovering the useful substance from the culture.

12. The method according to claim 11, wherein the useful substance is selected from the group consisting of amino acids, organic acids, nucleic acids, nucleic acid-related substances, sugars, lipids, vitamins, and pigments, and derivatives thereof.

13. The method for producing a useful substance according to claim 1, wherein the useful substance is a protein.

14. A plasmid, comprising the plasmid according to any one of claims 1 to 3, said plasmid having one or more genes integrated therein.

15. A method for integrating which comprises introducing the plasmid according to claim 14 to *Escherichia coli* W or *Escherichia coli* B, wherein said one or more genes are integrated into said *Escherichia coli* W or *Escherichia coli* B.

16. The method for integrating one or more genes according to claim 6, wherein the plasmid is integrated into a chromosome.

17. The method for integrating one or more genes according to claim 15, wherein the plasmid is integrated into a chromosome.

18. The method for integrating one or more genes according to claim 17, wherein a DNA fragment on the plasmid is substituted with a DNA fragment on a chromosome by homologous recombination.

19. A method for producing a useful substance, which comprises culturing the transformant according to claim 10 in a medium, allowing the useful substance to produce and accumulate in a culture and recovering the useful substance from the culture.

20. The method according to claim 19, wherein the useful substance is selected from the group consisting of amino acids, organic acids, nucleic acids, nucleic acid-related substances, sugars, lipids, vitamins, and pigments, and derivatives thereof.

21. The method for producing a useful substance according to claim 20, wherein the useful substance is a protein.

22. The plasmid according to any one of claims 1 to 3, wherein the *Escherichia* other than *Escherichia coli* K-12 is all *Escherichia* other than *Escherichia coli* K-12.

* * * * *

UNITED STATES PATENT AND TRADEMARK OFFICE
CERTIFICATE OF CORRECTION

| | |
|---|---|
| PATENT NO. | : 7,223,559 B2 |
| APPLICATION NO. | : 10/240712 |
| DATED | : May 29, 2007 |
| INVENTOR(S) | : Junicho Takano et al. |

It is certified that error appears in the above-identified patent and that said Letters Patent is hereby corrected as shown below:

ON THE TITLE PAGE ITEM [56] REFERENCES CITED:

Other Publications,
        After "Chen et al.": "Lethal is" should read --Lethal in--;
        After "Chen et al.": "Streptocococcus mutans" should read
            --Streptococcus mutans--
        "Furukawa et al. Breeding of L-threonine hyper-produced of E. coli W
            Appl. Microb. Biotechnol 1988vol. 29 253-257).*" should be
            deleted.
        After Chen, Anping, et al.,: "Definiciency" should read --Deficiency--;
            and
        After Chen, Anping, et al.,: "Lethal is" should read --Lethal in--.

COLUMN 2:

Line 24, "R-12" should read --K-12--; and
    Line 25, "unhoinogeneously" should read --unhomogeneously--.

COLUMN 3:

Line 24, "hydrolylazine" should read --hydrolylamine--.

COLUMN 4:

Line 8, "aother" should read --a other--.

COLUMN 7:

Line 50, "pXTS11910" should read --pMTS11910--.

COLUMN 10:

Line 2, "an" should read --on--; and
    Line 5, "detected. pTS14-LEUR122" should read
        --detected. ¶ pTS14-LEUR122--.

UNITED STATES PATENT AND TRADEMARK OFFICE
CERTIFICATE OF CORRECTION

PATENT NO. : 7,223,559 B2
APPLICATION NO. : 10/240712
DATED : May 29, 2007
INVENTOR(S) : Junicho Takano et al.

It is certified that error appears in the above-identified patent and that said Letters Patent is hereby corrected as shown below:

<u>COLUMN 11</u>:

Line 9, "to 2," should read --to claim 2,--;
Line 20, "Escherichi-" should read --Escherichia--; and
Line 21, "aother" should read --other--.

<u>COLUMN 12</u>:

Line 7, "claim 1, " should read --claim 11,--; and
Line 11, "integrating" should read --integrating,--.

Signed and Sealed this

Twenty-third Day of October, 2007

JON W. DUDAS
*Director of the United States Patent and Trademark Office*